United States Patent [19]

Guibert

[11] 4,307,286

[45] Dec. 22, 1981

[54] PULSATING HOT-AIR HEAT-UP SYSTEM

[76] Inventor: Raul Guibert, 9635 Oakmore Rd., Los Angeles, Calif. 90035

[21] Appl. No.: 97,787

[22] Filed: Nov. 27, 1979

Related U.S. Application Data

[60] Continuation-in-part of Ser. No. 971,381, Dec. 20, 1978, which is a division of Ser. No. 809,775, Jun. 24, 1977, Pat. No. 4,132,216, which is a continuation-in-part of Ser. No. 776,772, Mar. 11, 1977, Pat. No. 4,112,916.

[51] Int. Cl.$^3$ .................. A47G 23/04; F24C 15/32
[52] U.S. Cl. ............................ 219/400; 219/386; 126/21 A; 126/261; 99/480
[58] Field of Search ............... 219/400, 367, 369, 370, 219/386; 126/110 A, 21 A, 261, 285.5, 285 B; 99/480, 483, 487

[56] References Cited

U.S. PATENT DOCUMENTS

| 3,905,760 | 9/1975 | Johansson et al. | 219/400 |
| 4,089,322 | 5/1978 | Guibert | 126/261 |
| 4,132,216 | 1/1979 | Guibert | 126/261 |
| 4,160,440 | 7/1979 | Barnickle | 126/285.5 |

FOREIGN PATENT DOCUMENTS

| 1008343 | 5/1957 | Fed. Rep. of Germany | 219/369 |
| 2334285 | 1/1975 | Fed. Rep. of Germany | 126/21 A |

Primary Examiner—Arthur T. Grimley
Assistant Examiner—Bernard Boskoski
Attorney, Agent, or Firm—Michael Ebert

[57] ABSTRACT

A system for rapidly raising the temperature of a product having low thermal conductivity from a cold to a heated state in a manner bringing the internal temperature of the entire body of the product to substantially the same predetermined elevated temperature level. The system includes a chamber having a fluid-permeable product receiving section flanked by input and output plenums, and a main flow loop in which the chamber is connected in a continuous flow path in series with a heater station and an air pump in an arrangement in which air drawn from the output plenum and creating a negative pressure therein is conducted through the heater station and then forced in the heated state through an input line leading into the input plenum to create a positive pressure therein. The resultant pressure differential between plenums causes heated air to flow at high velocity through the section to heat the product therein. A bypass extending between the input to the heater station and the junction of the chamber and the pump in the main flow loop defines a feedback flow loop which excludes the chamber. A damper mechanism at this junction is cyclically operated to periodically block the flow of heated air into the chamber and to divert the flow into the bypass of the feedback loop for recirculating therein. As a consequence, main-loop flow through the chamber assumes the form of a pulsatory wave whose fluidic pulses have a peak temperature well above the predetermined level and whose relaxation periods are at a temperature below the predetermined level to promote rapid heat transfer in the body without, however, raising the surface temperature thereof above this level, the action continuing until the entire body of the product is at the desired level.

22 Claims, 17 Drawing Figures

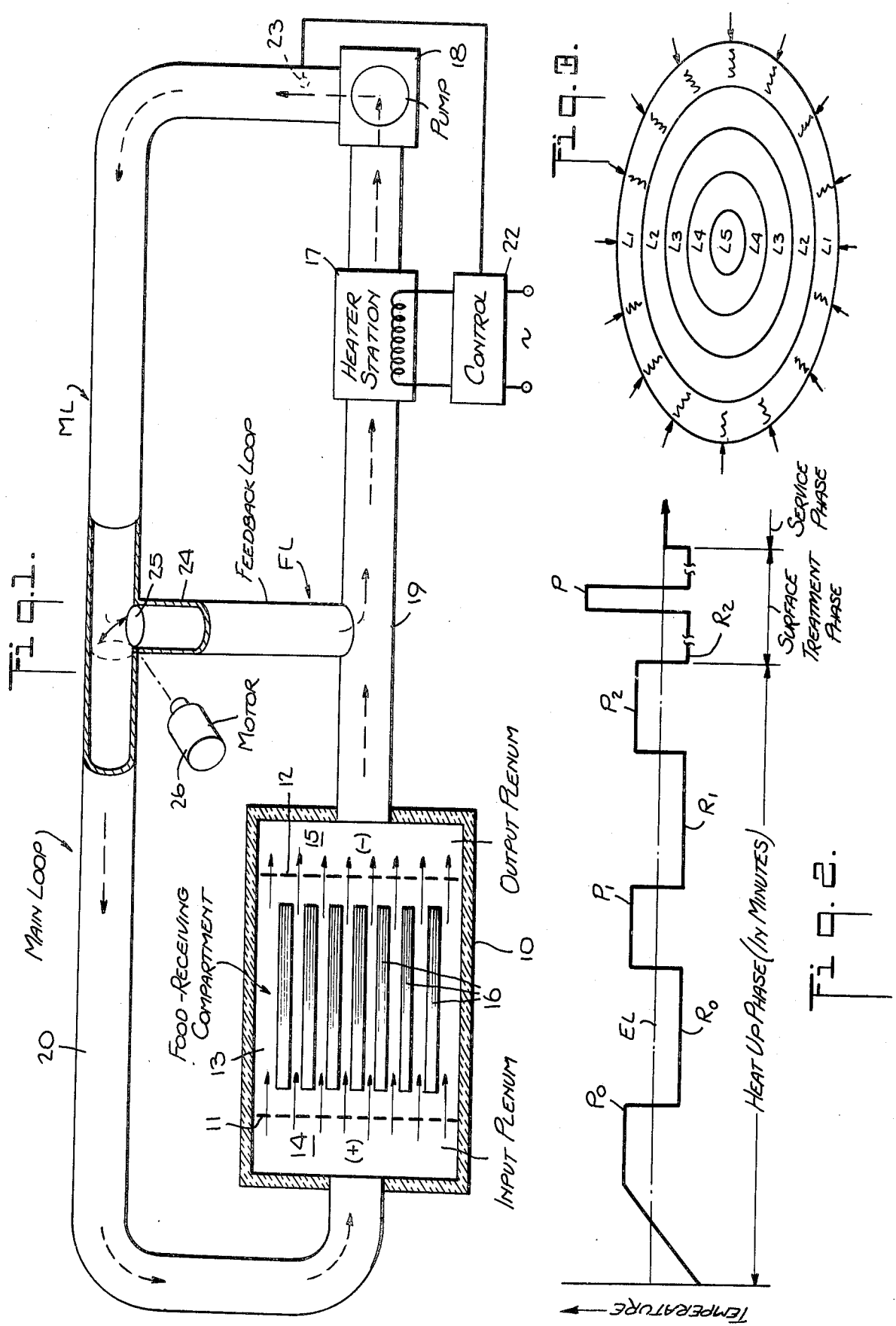

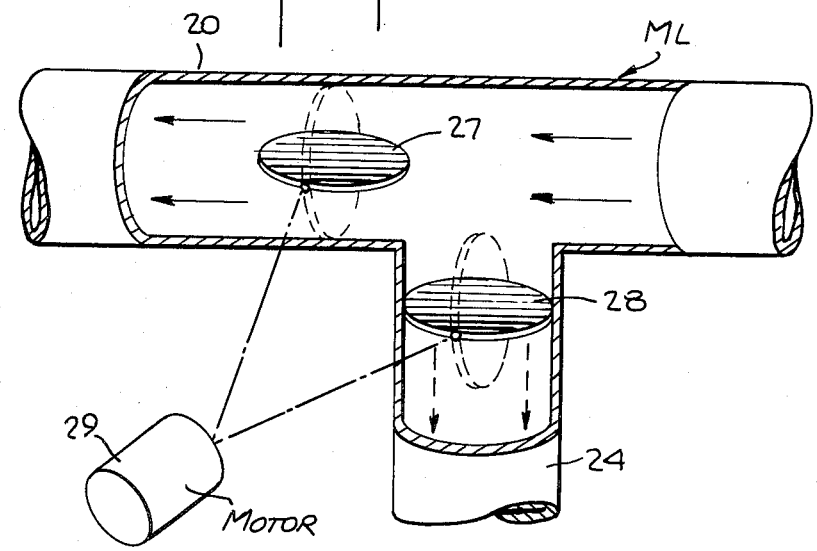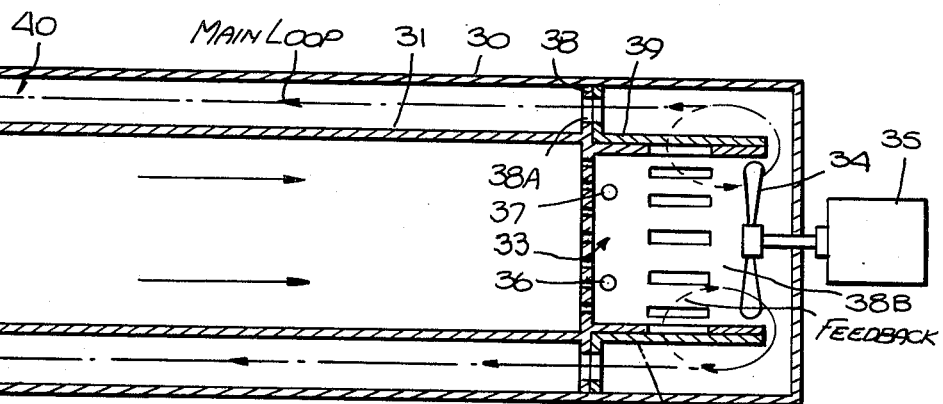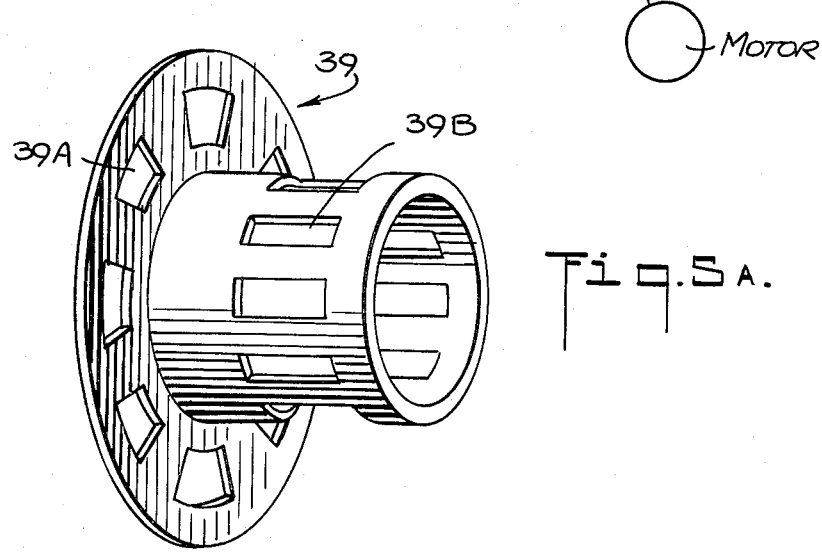

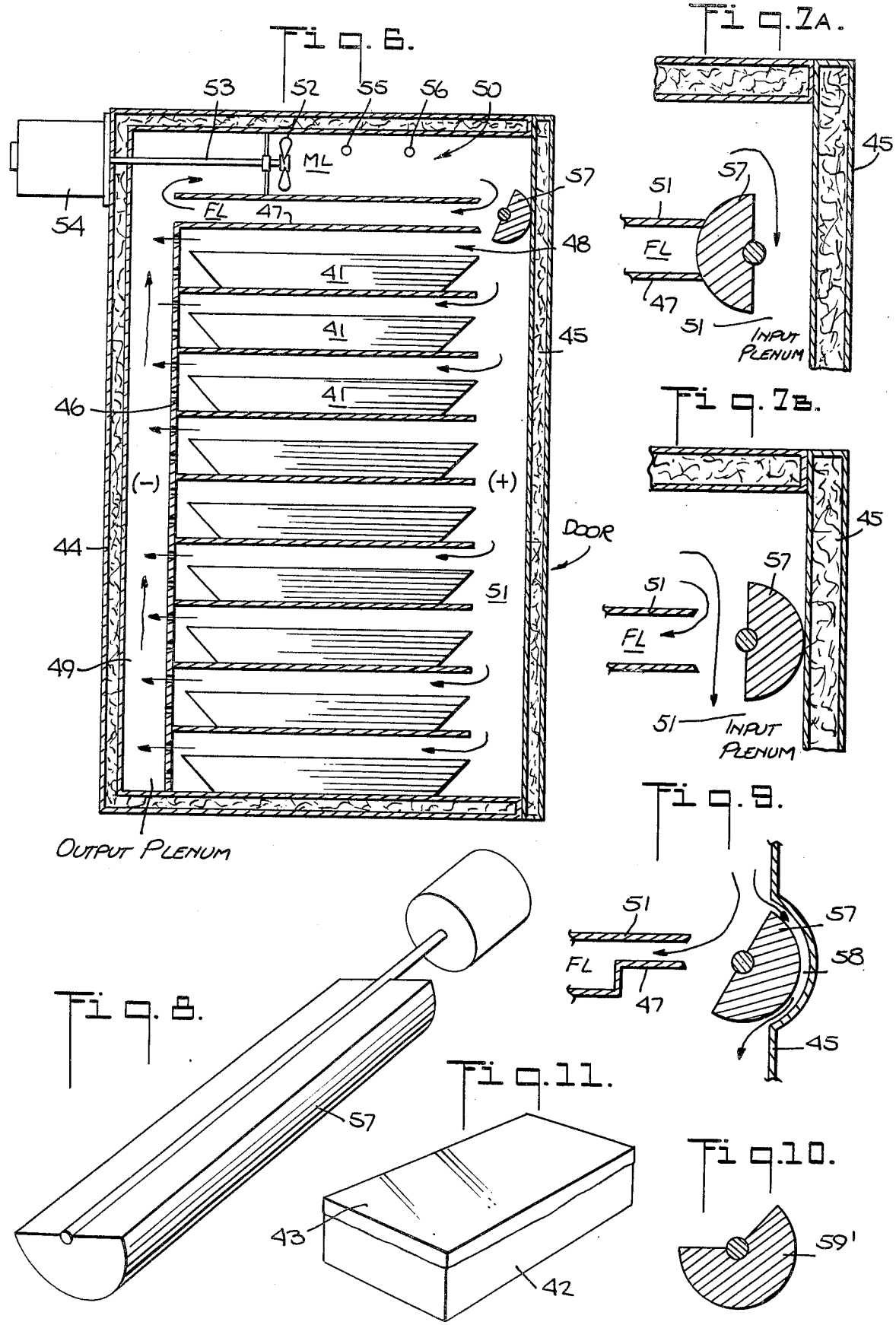

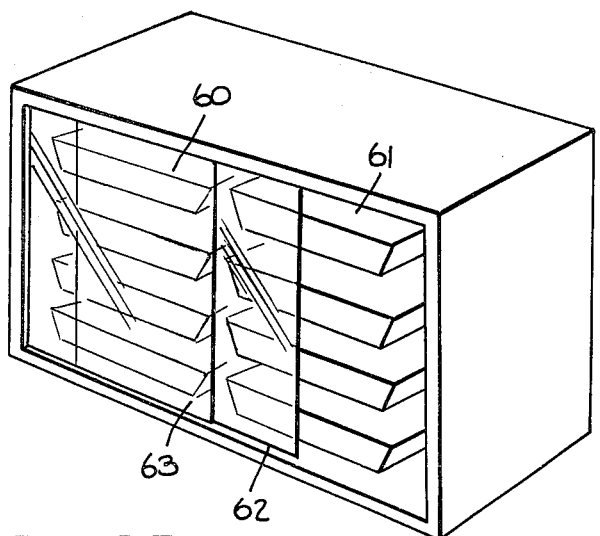
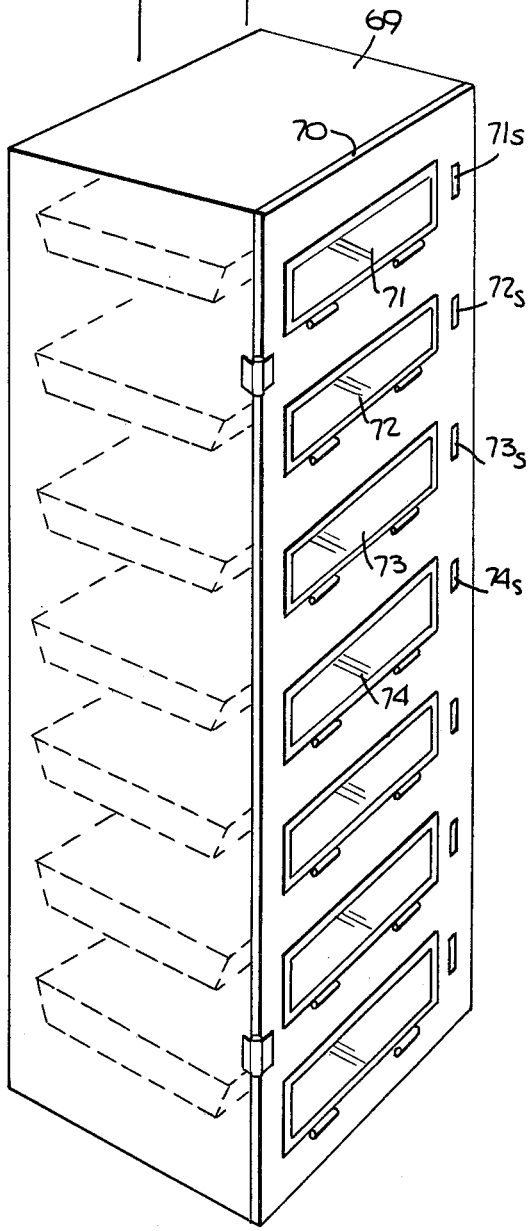
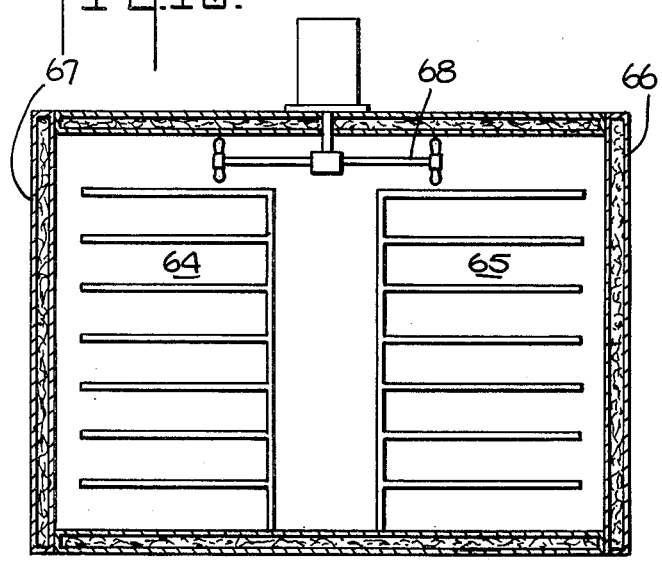
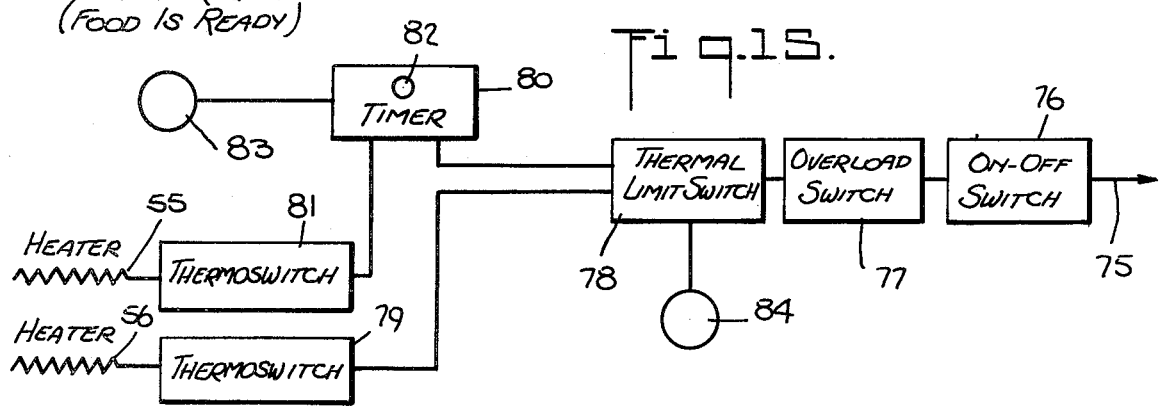

PULSATING HOT-AIR HEAT-UP SYSTEM

RELATED CASES

This application is a continuation-in-part of my co-pending application Ser. No. 971,381, filed Dec. 20, 1978, which is a division of an earlier application entitled "Two-Zone Hot Air Oven for Food Loaded Cartridges," now U.S. Pat. No. 4,132,216, dated Jan. 2, 1979, filed 6/24/77 as Ser. No. 5,809,775, which in turn is a continuation-in-part of an original application entitled "Hot Air Oven for Food-Loaded Cartridges," now U.S. Pat. No. 4,112,916, dated Sept. 12, 1978, filed 03/11/77 as Ser. No. 776,772. The entire disclosures of these related cases are incorporated herein by reference.

BACKGROUND OF THE INVENTION

This invention relates to a system for rapidly raising the temperature of a product having low-thermal conductivity from a cold to a heated state in a manner bringing the internal temperature of the entire body of the product to the same elevated temperature level, and more particularly to a system of this type for use in conjunction with a convenience food service technique wherein a meal is first cooked, then refrigerated and stored and subsequently reheated without degrading the basic texture, flavor and nutritional qualities of the meal.

To meet the growing need for quickly-prepared, low-cost meals, convenience food operations have been developed in which the food to be served is first cooked, then deep-freezed and stored. When an order is placed for a particular item on the menu, the selected item is withdrawn from the freezer, the frozen pre-cooked meal is then thawed and reheated.

In reheating a pre-cooked frozen meal in homes and restaurants, it is difficult, when going from the frozen state to an adequately heated service condition, to avoid a situation in which the core of the product is still cold even though the outer layer is quite hot. And when one seeks to ensure that the body of the food is hot throughout, there is a tendency to overheat the meal and thereby re-cook it, with a resultant loss of nutritional value and flavor.

In my related U.S. Pat. No. 4,112,916, "Hot Air Oven for Food-Loaded Cartridges" (hereinafter referred to as the Oven patent), there is disclosed a fast food service technique and apparatus therefore whereby pre-cooked food which has been refrigerated may thereafter be reheated and made directly available to customers without degrading the essential texture, flavor or nutritional qualities of the meal.

The Oven patent discloses a hot air oven for heating tray-loaded cartridges, each constituted by a stack of sealed trays containing pre-cooked meals nested within an open carton whose side walls have holes therein to admit heated air. The oven includes a rotating turntable provided with a raised annular shelf for supporting an annular array of cartridges, the side walls of which define a hollow center core. A driven propeller is disposed within the core, the space between the shelf and the turntable forming a restricted flow passage whose inlet communicates with the core and whose outlet lies at the periphery of the turntable.

In this hot air oven, a heater assembly above the annular cartridge array produces heated air which is blown by the propeller into the hollow core. Because of the flow restriction, a substantial portion of the heated air is forced through the holes of the cartons to heat the food in the trays. The remaining portion of the heated air passes through the flow passage, the air discharged from the outlet thereof being drawn upwardly by the suction force of the propeller to create an air curtain around the cartridge array. Thus a toroidal flow pattern of heated air fully envelops the heated trays and serves to isolate the trays from the relatively cool ambient air without, however, interfering with direct access to the trays which may be withdrawn from the cartons when the food is at the desired temperature level for service to diners.

In an oven of the type disclosed in my Oven patent, a two-section heating assembly is provided having different wattages, whereby at the outset of heating, both sections are operative for a controllable period, hereinafter called the heat-up phase, sufficient to raise the food temperature to the desired service level, after which the main section is rendered inactive while the auxiliary section, which draws much less power, then serves to maintain indefinitely the heated food at the proper level for service to diners, hereinafter called the "service phase."

During the heat-up phase, the rate of heat transfer from the hot air in the oven to the relatively cold food-loaded cartridges depends on the temperature differential; the greater the difference between the hot air temperature and the food temperature, the more rapid the rate of heat transfer.

Since the hot air temperature throughout the oven is at a fairly uniform level, the transfer rate at the outset of heating in the heat-up phase when both heater sections are operative is very rapid, but as the difference in temperature between the hot air and the food thereafter diminishes, the rate of transfer becomes increasingly slow and quite sluggish as the service temperature is approached.

Assuming that the food in the cartridges is initially at a temperature of about 10° F. and it is necessary to raise the food temperature to a service level of about 150° F. and further assuming a hot air temperature of about 165° F., then at the outset of the heat-up phase, there will be a sharp differential giving rise to very rapid heating. But as this temperature differential diminishes in the course of the heat-up phase, the rate of heat transfer slows down. When, for example, the food temperature reaches 130° F., the temperature differential relative to the heated air is only 35° F., and it takes a relatively long time before the food temperature can be raised to the service temperature of 150° F., at which point the heat-up phase is concluded and the service phase takes over with only one heater section operative to maintain this service temperature level.

Thus if one plots a curve of cartridge food temperature (10° F. to 150° F.) vs. time in the heat-up phase, the resultant curve for a hot-air temperature of 165° F. will exhibit a sharp rise from 10° F. to about 100° F. within a fairly short time interval, the curve thereafter leveling off as the temperature goes more gradually from 100° F. to 150° F. As a result, the duration of the heat-up phase is unduly prolonged, which in some situations may be a practical disadvantage.

If, for instance, a fast-food installation having a hot-air oven of the type disclosed in my Oven patent is loaded with cold food cartridges which must be made available for service to diners in about one hour after loading, this time may be inadequate to bring the food to its proper service level. If, therefore the cartridges containing the trays have just been removed from the freezer before being placed in the hot air oven, the necessary heat-up phase to raise the food temperature from, say, 10° F. to 150° F. with an oven of the type disclosed in this patent may be two hours or more, a period which is excessively long for some fast-food operations.

In order to provide an improved hot-air oven which affords a faster heat-up phase than an oven of the type disclosed in my Oven patent, my subsequent patent entitled "Two-Zone Hot Air Oven for Food-Loaded Cartridges" (hereinafter referred to as the Two-Zone patent) discloses an oven which functions to raise the food in the tray-loaded cartridges to a service temperature within a relatively short period.

In the Two-Zone patent, the hot-air oven is divided into a hot and an extra hot zone such that as the tray-loaded cartridges containing pre-cooked meals are carried by a turntable cyclically through these zones, the extra-hot zone acts to maintain a marked temperature differential between the temperature of the food trays and the hot air even as the food approaches the service temperature, whereby the transfer rate is rapid throughout the entire heat-up phase without, however, unduly heating the material of the trays.

In a hot-air oven for heating food-loaded cartridges of the type disclosed in my Two-Zone patent, each cartridge is formed by a stack of sealed trays all containing a pre-cooked meal, the stack being nested within an open carton whose side walls have holes therein to admit heated air. The oven includes a rotatable turntable provided with a slightly-raised annular shelf for supporting an annular array of cartridges forming a hollow center core whose boundary is defined by the walls of the cartons. Within the core is disposed a driven propeller, the space between the shelf and the turntable forming a restricted flow passage whose inlet communicates with the hollow core and whose outlet lies at the periphery of the turntable.

A heater assembly mounted above the cartridge array produces heated air which is blown by the propeller into the hollow core. Because of the flow restriction and the configuration of the carton walls, a substantial portion of the heated air is forced through the holes in carton walls in the cartridge array to heat the food in the trays, the remaining portion passing through the flow passage. The heated air escaping from the outlet of the flow passage is drawn upwardly by the suction force of the propeller to create an air curtain around the cartridge array which returns the air to the heater assembly for reheating and recirculation. The air curtain is surrounded by a thermal barrier having a front access port therein to provide access to the interior of the oven whereby cartridges may be inserted in the oven when loading the shelf and selected trays may be withdrawn therefrom when dispensing meals to diners.

The heater assembly is constituted by two concentric arcuate sections of different capacity, both of which are initially energized to raise the oven temperature to a high level and to bring the food to the desired service temperature in the course of a heat-up phase, after which the larger capacity main section is cut off automatically by means of a timer, whereby the food in the oven is thereafter maintained at the desired level during a service phase by the smaller auxiliary section.

Thus a toroidal flow pattern of heated air is created which fully envelops the annular array of cartridges and serves to isolate the trays from the relatively cool ambient air, without, however, interfering with direct access to the trays which may be withdrawn from the cartons through the access port when the meals are at the desired service temperature.

In order to accelerate the rate in the heat-up phase at which the food is raised to its service temperature, disposed within the hollow core of the oven in the sector thereof facing the access port is an arcuate shield which acts to restrict the passage of heated air through the holes of cartons in the shielded sector of the core so that as the turntable rotates, the cartridges are subjected to heated air from the core only when they travel through the unshielded sector.

As a result, the oven is effectively divided into a shielded hot zone and unshielded extra-hot zone, the heater arrangement being such that the temperature in the extra-hot zone is well above the service food temperature and is even above the softening point of the plastic trays. But because the turntable during each cycle of rotation at 1 RPM carries the cartridges from the extra-hot zone to the hot zone whose temperature is below the softening point of the trays, the trays never reach their softening point in the course of the relatively short heat-up phase.

The two-zone oven accelerates the food heating process; for even when the food temperature approaches the service temperature, there is still a marked temperature differential between the food temperature and the super-hot temperature to promote more rapid heat transfer. Thus instead of a time-temperature curve in the heat-up phase which rises steeply and then gradually levels off, the curve remains relatively steep throughout the entire heat-up phase, thereby shortening the duration of the heat-up phase.

Though the technique disclosed in my Two-Zone patent is adapted to rapidly heat-up pre-cooked food to a service temperature and to thereafter maintain the food at this temperature, the generally-cylindrical oven structure which includes a turntable for carrying out this technique is designed to handle a large volume of food-loaded cartridges. This structure can be scaled down to create a small unit suitable for home use operating on the same principles. But a cylindrical unit, in many instances, does not lend itself to a home or other installations having space restrictions.

In a typical domestic kitchen, a box-like unit for reheating frozen pre-cooked food packages is more appropriate. Box-like home units operating a convection heating principles are known and are commercially available. However, such units are incapable of rapidly heating up trays or containers of pre-cooked food and thereafter maintaining the food at a desired service temperature.

In convection-heating home units of the type heretofore available, one can set the oven for a desired heat-up temperature. But as previously explained, the temperature differential between the cold food and the heated air is large only in the initial heat-up period, and the closer the food approaches the service temperature, the smaller the differential and the slower the rate of heat transfer. Consequently, it takes an unacceptably long time for the food to reach the service temperature. This is particularly the case when the unit is fully loaded with several trays or packages of frozen food.

If the operator of the typical home unit tries to accelerate the heat-up phase by setting the temperature level of the oven well above the service temperature, the resultant heating will generally be destructive of the food; for the outer layers of the food will then be heated to an excessive level, causing these layers to be recooked or burned.

Again, it must be borne in mind that frozen food has poor thermal conductivity; hence the rate of heat transfer within the body of the food is slow. If, therefore, one subjects a body of frozen food to a continuously maintained high temperature, the outer layers of the body will undergo rapid heat transfer and become overheated before significant heating takes place in the inner regions of the body.

SUMMARY OF THE INVENTION

In view of the foregoing, the main object of this invention is to provide a system adapted to rapidly raise the temperature of pre-cooked food or other product having low thermal conductivity from a cold or frozen state to a heated state in a manner bringing the internal temperature of the entire body of the product to substantially the same predetermined elevated temperature level, the product thereafter being maintained indefinitely at the elevated temperature without overcooking the product.

More particularly, an object of this invention is to provide a system of the above type in a highly compact and efficient arrangement which is suitable for home use or in any other environment, and having relatively low energy requirements.

A significant aspect of the present invention is that the system may be embodied in various practical configurations, depending on its end use. Thus the system may be embodied in a box-like unit that is best suited for home use and occupying no more space than a conventional microwave oven or convection heating unit. Or the unit may take the form of a tall, narrow box having a vertical series of hinged windows providing access to individual packages of pre-cooked food, this unit functioning as a vending machine.

Also an object of the invention is to provide a system of the above type in which the pre-cooked cold food product during the heat-up phase is raised in temperature by periodic pulses of hot air which flow past the food packages at high velocity, the temperature of the pulses being well above the predetermined elevated service temperature level, whereby the temperature differential between the heated air and the food is high even when the food approaches the service temperature level, thereby effecting a high rate of heat transfer and causing the food to reach the service temperature level quickly without, however, excessive heating thereof.

Yet another object of the invention is to provide a pulsed hot-air heating system which operates reliably and efficiently and which may be manufactured on a mass production basis at low cost.

Briefly stated, in a hot air heating system in accordance with the invention to rapidly raise the temperature of pre-cooked food or other product having low thermal conductivity from the cold or frozen state to a service temperature at a predetermined elevated temperature level at which the food is in condition to be served, and to maintain the food at this level until there is a demand therefor, there is provided a thermally-insulated chamber having a fluid-permeable product receiving section flanked by input and output plenums.

A main flow loop is provided in which the chamber is connected in a continuous flow path in series with a heater station and an air pump or blower in an arrangement in which air drawn via an output line from the output plenum and creating a negative pressure therein is conducted through the heater station and then forced in the heated state through an input line leading into the input plenum to create a positive pressure therein. The resultant pressure differential between the plenum causes heated air to flow at high velocity through the section to heat the product contained therein.

A by-pass extending between the input to the heater station and the junction of the chamber and the pump in the main flow loop defines a feedback flow loop which excludes the chamber. A damper mechanism at this junction is cyclically driven to periodically block the flow of heated air through the main loop into the chamber and to divert the flow into the feedback loop for recirculation therein.

As a consequence, main loop flow through the chamber assumes the form of a pulsatory wave whose fluidic pulses have a peak temperature whose level is well above the predetermined temperature level and whose relaxation periods are at a temperature below this predetermined level, thereby promoting rapid heat transfer in the body of the product without, however, raising the surface temperature thereof above this level. This action is continued until the entire body of the product is at the desired service temperature level, at which point the system is operated to maintain this level indefinitely without overheating the food product.

OUTLINE OF DRAWINGS

For a better understanding of the invention as well as other objects and further features thereof, reference is made to the following detailed description to be read in conjunction with the accompanying drawings, wherein:

FIG. 1 schematically illustrates a pulsatory wave heating system in accordance with the invention;

FIG. 2 is a waveform representing different operating phases of the system;

FIG. 3 is a sketch showing a body of food subjected to pulsatory heat;

FIG. 4 illustrates an alternative form of damping mechanism;

FIG. 5 schematically illustrates a compact version of a system according to the invention;

FIG. 5A is a perspective view of one shutter element of the damper mechanism included in the FIG. 5 section;

FIG. 6 is a schematic view, in longitudinal section, taken through a preferred embodiment of a pulsed hot air heating unit based on a system in accordance with the invention;

FIGS. 7A and 7B are sketches which serve to explain the operation of the rotating gate included in the FIG. 6 unit;

FIG. 8 is a separate perspective view of the rotating gate included in the FIG. 6 unit;

FIG. 9 is a modification of the unit providing a leakage path for heated air into the input plenum;

FIG. 10 is a modified gate configuration;

FIG. 11 is a perspective view of one form of food package suitable for the unit;

FIG. 12 shows another embodiment of a home unit;

FIG. 13 is a double unit in accordance with the invention;

FIG. 14 is a unit in a vending machine configuration; and

FIG. 15 is the electrical system associated with the unit.

DESCRIPTION OF INVENTION

The Basic System

Referring now to FIG. 1, there is shown a system in accordance with the invention for rapidly raising the temperature of a pre-cooked meal or other product having low thermal conductivity from a cold or frozen state to a heated state in a manner bringing the internal temperature of the entire body of the product to substantially the same predetermined temperature level, the internal temperature of the product thereafter being maintained at the desired level for an indefinite period.

Thermal conductivity is defined by the quantity of heat which flows in unit time through a unit area of a plate of unit thickness having unit differences of temperature between its faces. There is no generally accepted combination of units for expressing thermal conductivity. One common combination of units for stating thermal conductivity is in British units where $k = BTU/(ft^2)$ (h) for 1-inch thick plate/F°.

In British thermal units, the thermal conductivity of silver at room temperature is 2824, which is very high; whereas that of ice is 15, which represents a quite low value of thermal conductivity. Frozen or refrigerated food has a low value thermal conductivity close to that of ice. Since the rate at which heat is conducted through a body is a function of its thermal conductivity, it is evident that heat is conducted at a much faster rate through silver than through frozen food. The manner in which a system in accordance with the present invention accommodates itself to the low conductivity of the product being heated to effect rapid heat of the product without overheating thereof will be later explained.

And since a system in accordance with the invention makes use of heated air, the distinction between natural and forced convection must be understood. Natural convection is a transfer of heat to and from a surface by the movement of a fluid when this movement is caused solely by a difference in fluid density. But in forced convection, the velocity of the fluid is a dominant factor for heat transfer. The present invention makes use of forced convection with respect to all sides of the food body being heated to effect heat transfer at a very rapid rate.

The system illustrated in FIG. 1 includes a thermally-insulated chamber 10 which is divided by fluid-permeable partitions 11 and 12 or other means into a product-receiving compartment or section 13 flanked by an input plenum 14 and an output plenum 15. Placed in section 13 are cold or frozen pre-cooked food packages 16 which are stacked therein with air spaces separating the packages to permit the flow of heated air through the compartment in intimate contact with the food packages therein, which flow serves to heat the package contents at a rapid rate.

In practice, section 13 may contain shelves to receive the food packages or whatever other product is placed therein. The products are contained in trays or cartridges or are in loose form. Assuming a commodious compartment with an access door, the food packages may be carried by a cart wheeled into the compartment, or it may be brought therein by a conveyor. In the generalized system shown in FIG. 1, the food or other low thermal conductivity product may be placed in section 13 in any appropriate arrangement which permits a flow of air through the food packages from input plenum 14 through section 13 into output plenum 15.

Chamber 10 is included in a main flow loop ML wherein the chamber is connected in a continuous flow path in series with a heater station 17 and an air pump or blower 18. The main loop configuration is such that air drawn by pump 18 from output plenum 15 via an output line 19 and creating a negative pressure therein is conducted through heater station 17 and then forced in the heated state through an input line 20 leading into the input plenum 14 to create a positive pressure therein. The resultant pressure differential between plenums 14 and 15 causes heated air to flow at high velocity through the compartment to rapidly heat the product therein by forced convection.

Heater station 17 may be in any known form; hence heat may be transferred to the air passing therethrough by electrical heater elements or by a hot water or steam heater. To simplify the disclosure, we shall assume an electrical heater element 21 to which power is supplied by an electronic control unit 22 responsive to a thermal sensor 23 in the main loop, the control unit acting to maintain the air temperature in this loop at a desired level.

Extending between the input to heater station 17 in line 19 and the junction of pump 18 and chamber 10 in the main loop is a by-pass 24 which defines a feedback loop FL which excludes the chamber so that when the feedback loop is operative, the heated air is continuously recirculated therein.

At this junction there is installed a damper mechanism 25 which is shown in a simplified version as a pivoted damper element cyclically operated by a motor 26 or other suitable drive means so that in the course of each operating cycle, element 25 is first positioned to block flow into by-pass 24 whereby the heated fluid then flows entirely through main loop ML, in which case flow passes through chamber 10 and then swings 90 degrees to block flow into input line 20 and divert the heated air into feedback loop FL.

The periodically-operated damper mechanism which functions in the course of each cycle to switch flow from main flow loop ML to feedback loop FL may take many forms other than the simple pivoted element shown in FIG. 1. Thus as shown in FIG. 4, instead of a single pivoted damper element, one may employ a pair of rotating elements 27 and 28 at the junction of the main loop ML and the feedback loop FL, element 27 being placed in the main loop and element 28 in the feedback loop. Both elements are driven by a common motor 29 through suitable gear cams in a phase relation such that when element 27 is fully open to allow fluid through the main loop element 28 is then in its fully closed position to block flow through the feedback loop.

As a consequence of this damper operation, the flow of heated air through main loop ML in the heat-up phase, as shown in FIG. 2, assumes the form of a pulsatory wave whose fluidic pulses $P_1$, $P_2$, etc. have a peak temperature well above the predetermined temperature level represented by dashed line EL to which the internal body temperature is to be raised from the cold state. The relaxation periods $R_1$, $R_2$, etc. between pulses are at oven temperature which though above the initial cold temperature of the product, is well below the predetermined elevated temperature level due to the cooling action of the product being processed. The first pulse $P_o$ in the waveform has a sloping leading edge which represents the initial start up of the heater station.

The pulsatory heat-up phase, which may last a half hour or longer, depending on the product load and its initial low temperature, promotes rapid heat-transfer without, however, raising the surface temperature of the body of the product above the predetermined elevated level. Thus in the heat-up phase, the temperature of the product is never in the case of pre-cooked food raised to a level that would cause the food to be re-cooked.

However, in some instances, as with meat roasts, fried food such as fish or pastry products such as pies, it may be desirable upon completion of the heat-up phase or at some point in the heat-up phase to treat the surface of the food as to bake or otherwise treat the food surface or crust. For this purpose, the system may include a brief surface-treatment phase in which the peak temperature level of the pulses $P_S$ are very high, well above the peak temperature of the pulses in the heat-up phase. This phase is followed by a steady service phase in which the heater station is thermostatically controlled to take into account heat losses from the chamber and to maintain the internal temperature of the product at the elevated temperature level EL for an indefinite period. While the surface treatment phase is shown in FIG. 2 as interposed between the heat-up and the service phases, in practice, it may be placed within the heat-up phase near the conclusion thereof or at any other point therein.

While FIG. 1 shows a square wave pattern, in practice, depending on the nature of the damper mechanism, the wave formation may be sinusoidal or in any other pulsatory form, so that instead of a steep or abrupt transition from the relaxation to the peak temperature level, the transition is caused to follow a rising slope or curve.

Operation

The heat-up phase in a system in accordance with the invention is of relatively short duration for food products and may be in a range of ½ hour to an hour, depending, of course, on the magnitude of the food load placed in the unit and the initial cold temperature of this load. The reason the heat-up phase is brief is that the rate of heat transfer is fast throughout this phase, not merely at the outset of this phase.

In contradistinction, in a continuously-heated conventional oven, if the oven temperature is maintained at a substantially very high level to effect rapid heat-up of the pre-cooked food, the temperature will then be such as to cause undesirable recooking of the food. And if the oven temperature is maintained at a much lower constant level to heat up the food without recooking thereof, then the heat-up period becomes unduly prolonged. With the present system, which makes use of a pulsatory heat wave in a forced convection arrangement, the rate is rapid for the entire range of food temperatures, running from an initial cold temperature to a hot service temperature level at the completion of the heat-up phase without danger of re-cooking the food despite the high peak temperature of the pulses.

Because the hot air temperature of the pulsed air in the heat-up phase is significantly higher (i.e., 190° F.) than the food service temperature level (i.e., 150° to 160°), even though the temperature differential between the hot air temperature and the prevailing food temperature is greatest at the outset of the heat-up phase, it never reaches a condition where this differential is small. Even as the food temperature approaches the service temperature, say, at 135° F. the differential between the then prevailing temperature and the hot air temperature remains fairly large and the rate of heat transfer is therefore still quite rapid.

Hence, instead of having a food temperature vs. time curve for the heat-up phase—which is steep for the first 10 minutes or so of heat-up and then proceeds to level off to a degree that it takes an extended time to raise the temperature of the food to the service level—with the pulsed air technique in accordance with the invention, though the curve becomes somewhat less steep as one approaches the service level, at no time does the curve reflect a slow heat-up rate.

The rate of pulsing is a critical aspect of the present invention; for as shown in FIG. 3, a body of cold or frozen food may be regarded as formed of a succession of layers going from the outer surface to the core, as indicated by layers $L_1$ to $L_5$, layer $L_1$ being the outer layer and $L_5$ the core layer. The core can only be heated by transmitting heat through successive layers of poor thermal conductivity from the exterior to the interior.

Assuming, therefore, that the outer layer is initially at 10° F. and is subjected for about one minute to a hot air pulse ($P_1$, $P_2$, etc.) having a temperature of 190° F. (one half cycle) and the velocity of hot air flowing past the body of the food is such as to raise the temperature of the outer layer to, say, 20° F., then in the next half cycle (represented by relaxation intervals $R_1$, $R_2$, etc.) which also lasts about a minute and in which the air is quiescent, heat from the 20° F. outer layer $L_1$ is transferred to the second layer $L_2$ which is thereby raised in temperature from 10° F. to 15° F., with a resultant reduction in temperature of the outer layer to, say, 15° F. Thus the interval between hot air pulses represents a dwell or relaxation period during which interval heat transfer takes place in the cold food body.

When outer layer $L_1$, now at 15° F., is subjected to the next hot air pulse at 190° F. for a minute, this will raise the temperature of the outer layer to, say, 25° F.; and during the next minute interval when the air is again quiescent, there will be a heat transfer from the outer layer to the second layer $L_2$, this time raising the temperature of the second layer to 20° F. and reducing the outer layer to 20° F. It is to be understood that these temperature values are but one example of a usable pulsatory heat wave and that in practice the damper mechanism may be constructed and operated to provide a desired relation between the peak temperature of the pulses and the temperature level of the relaxation periods and to provide any desired relation between the duration of the pulses and that of the relaxation periods.

Similar heat transfer actions take place concurrently between the second and third layers $L_2$ and $L_3$ and between the third and fourth layers $L_3$ and $L_4$ and so on, very much in the fashion of an electronic cascade counter. In a counter, when an input signal (a heat pulse) is received, the state of each stage (i.e., layer) in the cascade is advanced in an ordered sequence. Thus the intervals between hot air pulses applied to the outer layer of the cold body allow time for transfer of heat to be effected from layer to layer. Because the outermost layers which are subjected to a temperature well above the service temperature are permitted to cool down in these intervals, the temperature of these layers is never permitted to rise above the service temperature and excessive heating is avoided.

The relative duration of pulses $P_1$, $P_2$, etc. and relaxation periods $R_1$, $R_2$, etc. is selected in accordance with the thermal properties of the food load and its rate of internal heat transfer and can be adjusted to accommodate the system to the nature of the load.

While the system is described herein as adapted to raise a cold product to a heated condition using air as a fluid, the same basic system is operable using liquid as the fluid. Thus in the case of food which is non-reactive with water or with food contained in liquid-impermeable pouches, heated water may be used as the fluid medium. Also, the system may be arranged to operate in reverse to that shown herein to reduce the temperature of an initially hot product to a cold state, in which event instead of a heater station, use is made of a cooling or cryogenic station, the operating principles being essentially the same.

1st Compact System

The basic system shown in FIG. 1 may be constituted by a chamber 10 located at a convenient site, and a heater station 17 and pump 18 placed at another site and linked to the chamber by flexible ducts or fluid lines which define the main and feedback flow loops. Thus the chamber is totally free of working equipment and can readily be disconnected from the ducts for cleaning, repair or any other purpose. Or the chamber may be in the form of a shipping box which is transported to a site having a permanent installation of a heater station and blower or pump, the box being disconnected from the lines when the products therein are consumed and being returned to a commissary for reloading.

In some cases, it may be desirable to incorporate all components of the entire system in a single, highly compact structure. An arrangement of this type is shown in FIG. 5 wherein a box 30 is provided with an interior product receiving cylindrical compartment 31 which is so held within the box as to define an input plenum 32 and an output plenum 33. Output plenum 33 leads into an end region having a fan 34 therein operated by an external motor 35. Placed in output plenum 33 are electrical heater elements 36 and 37.

A rotary damper mechanism is provided with a stator 18 and a matching rotor 39, the latter being shown separately in FIG. 5A. Stator 38 is provided with a disc section having an annular array of apertures 38, 39 therein, providing access to a main loop passage 40 defined between cylindrical compartment 31 and box 30. Stator 38 is also provided with a tubular section at right angles to the disc section and having a circumferential array of apertures 38B therein. Rotor 39 is provided with a corresponding disc section having apertures 39A therein and a corresponding tubular section having apertures 39B therein.

The apertures in the disc and tubular sections of the rotor and stator of the damper mechanism are out of phase with each other so that when at an angular position of the rotor relative to the stator at which the apertures of the disc sections lie in registration, the apertures in the tubular sections are then out of registration.

In operation, air is drawn by fan 34 from output plenum 33 to create a negative pressure therein and is blown by fan 34 through main loop duct 40 into input plenum 32 to create a positive pressure therein, this occurring when in the course of each rotary cycle of the damper mechanism the apertures of the disc section of the stator and rotor are in registration. The resultant pressure difference between plenums causes air to flow at high velocity through compartment 31 containing cold food products to be rapidly raised in temperature.

The air flowing from compartment 31 into output plenum 34 is heated by electrical element 36 and 37.

When however, the damper mechanism in the course of each rotary cycle has its tubular section apertures in registration and its disc section apertures out of registration, the flow of heated air through main loop duct 40 is blocked, the flow then going through the registered apertures of the tubular sections back into output plenum 33 to create a feedback loop in which air is continuously recirculated through the heater elements.

Thus the operation is essentially the same as in FIG. 1, for the air fed through the food compartment has a pulsatory form. The relationship of the peak pulse temperature and the temperature of the relaxation intervals to the predetermined elevated temperature level of the product is the same as in FIG. 1.

Second Compact System

Referring now to FIG. 6, there is shown another form of unit compact system in accordance with the invention which operates on the pulsed hot-air principle and functions to rapidly heat up a load of cold or frozen pre-cooked food packages 41. These packages or food containers are stacked vertically within the unit, with air spaces separating the packages to permit the flow of hot air in the spaces between packages.

In practice, the packages may be constituted by covered trays in which the tray and the cover therefor are both fabricated of a synthetic plastic material, such as polyethylene, acceptable for and non-reactive with food, the material being capable of withstanding the wide range of temperatures involved in refrigerating and reheating the food contents to a service temperature. By service temperature is meant a food temperature which is below the temperature at which food boils or otherwise cooks and yet is high enough to cause the food, when served to a customer, to be regarded as "hot off the oven".

The tray cover is preferably formed of lower density material than the tray so that it is more flexible than the tray and can be pried off without difficulty.

Alternatively, as shown in FIG. 11 each package may be constituted by a cardboard tray 42 whose inner face has a plastic film laminated thereto to render the tray impermeable to liquid, the tray being covered by a removable transparent plastic film 43 which visually exposes the pre-cooked meal contained in the tray.

The unit is adapted to raise the temperature of the food contents to a suitable service level in the range of about 150° to 170° F., and to then maintain this temperature with a minimal amount of heat loss. The energy requirements for the unit are relatively low, for reasons to be later explained.

The unit is formed by a thermally-insulated box 44 having a thermally-insulated front access door 45 hinged thereto. Created within box 44 by means of a perforated back partition 46 in parallel relation to the back wall of the box and an upper wall 47 in parallel relation to the top side of the box is an inner chamber 48 which is dimensioned to accommodate the stack of food packages 41. In practice, inner chamber 48 may be provided with wire-formed shelves or other expedients to support the packages one above the other, with the required air spaces therebetween.

The free space between back partition 46 of the inner chamber and the back side of box 44 defines an output plenum 49. The free space between upper wall of the inner chamber and the top side of the box constitutes the duct 50 of a main flow loop ML, while the free space between door 45 and the open front of inner chamber 48 defines an input plenum 51.

Disposed in duct 50 in parallel relation to the upper wall 47 of the inner chamber is a horizontal septum which defines a bypass forming feedback loop FL. A fan propeller 52 supported on a shaft 53 driven by a motor 54 mounted externally on the back side of box 13 operates within duct 50. This fan acts to draw air from output plenum 49 to create a negative pressure therein and to force the drawn air into input plenum 51 to produce a positive pressure therein, the resultant pressure differential causing heated air to flow at high velocity through the inner chamber 48 to heat the food therein.

Disposed in the flow path of the air blown by fan 52 in duct 50 are electrical heater sections 55 and 56. Section 55 is a high wattage heater and section 56 an intermediate wattage heater, so that the air blown through duct 50 into input plenum 51 is raised in temperature to a degree determined by these heaters.

Mounted for rotation at the junction of the main loop ML and the feedback loop FL is a gate-type damper mechanism in the form of a semi-cylindrical roll 57 which is driven through a suitable bear train by motor 54 or by a separate motor. In the course of each revolution, gate 57 goes from a zero angular position in which hot air from the main loop duct 50 is blown into input plenum 51, while feedback loop FL is fully blocked, as shown in FIG. 1A, to a 180° position in which both feedback loop FL and input plenum 51 are unblocked, as shown in FIG. 7B.

The relative amount of hot air going to the feedback loop and to the input plenum is modulated in accordance with the angular position of the gate in the course of each operating cycle. As a consequence, the amount of air fed into input plenum 51 goes periodically from zero to maximum in accordance with a sinusoidal or some other curve representing this activity, depending on the geometry of the gate with respect to the feedback and main loop passages controlled thereby.

Thus in the course of each gate cycle, which in practice has a two-minute duration, when roll 57 is rotated at a rate of 2 rpm, the hot air is more or less fed into input plenum 51 in the main loop ML or into feedback loop FL. When directed into the feedback loop, the hot air from duct 50 is recirculated through the heaters. The recirculation of the air, when directed through the feedback path, prolongs the exposure of the air to the heater elements and serves, therefore to raise its temperature despite the short length of duct 50. Because the air flow through the main loop is periodically blocked, the hot air fed therethrough is pulsatory in nature, in accordance with the principles underlying the basic system as explained in connection with FIG. 1.

The operation of the unit shown in FIG. 6 involves a rapid heat-up phase in which the food in cold packages 41 are raised in temperature until they reach their service temperature. The necessary heat energy for this purpose is generated by the main or high-wattage electrical heater section 55. After the food is at the service temperature, this temperature is thermostatically-maintained within the unit by the auxiliary of intermediate wattage heater section 56 for a service phase whose duration is indefinite.

In both the heat-up and service phase, fan 52 functions to suck air from output plenum 49 and to draw this air through duct 50 of the main loop ML where the air is heated by the operating heater section before it is forced into input plenum 51 to create a hot air curtain therein. Because of this action, output plenum 49 is under negative pressure while input plenum 51 is under positive pressure to produce a pressure differential therebetween.

Since perforated partition 46 of inner chamber 48 separates output plenum 49 from input plenum 51, air from the hot air curtain under positive pressure in the input plenum is forced laterally through the inner chamber where it passes through the free spaces between packages 41, the air then going through the openings in partition 46 into the output plenum to complete the flow cycle.

In the course of this cycle, the heated air going through the inner chamber is cooled by the cold packages, so that the air is returned to the output plenum in relatively cool condition. In practice, the size of the openings and the pressure differential created by the suction force are such as to produce a hot air velocity through the inner chamber of approximately 1000 FPM.

During the heat-up phase when heater element 55 is energized, gate 57 is caused to rotate to periodically admit pulses of heated air into the input plenum. The temperature of these hot-air pulses, as determined by heater element 55, is well above the desired service temperature. Assuming, therefore, a service temperature of about 150° F., the peak temperature of these pulses will be about 190° F.

In the FIG. 6 arrangement, rotating gate 57 acts to periodically cut off the flow of hot air into the main flow loop and to divert the air into the feedback loop so that the temperature of air in the main loop abruptly rises from a minimum level to a maximum level in the course of each operating cycle. It may be desirable to bias this minimum level upwardly to reduce the spread between the levels. Such biasing is effected by providing a leakage path 58 as shown in FIG. 9, by means of a convex bulge in door 45 whose contour follows that of the gate roll 57 so that regardless of the angular position of the roll, some hot air from the upper air space leaks into the front air space enough to take care of the heat losses of the unit.

Roll 57 need not be in the form shown in FIG. 8, where the roll has a semi-circular cross section to provide open and closed segments of equal size. Thus the geometry of the roll may be that of roll 59 shown in FIG. 10 where the closed segment is larger than the open segment. By such geometric changes, one can obtain whatever hot-air pulse wave pattern is desired.

Other Embodiments

In the unit shown in FIG. 6 a single high stack of food packages is accommodated in the inner chamber of the box, access to these packages being had by opening the front door. Because of the air curtain overlying the open front of the inner chamber, heat losses resulting from opening the door are minimized.

The unit illustrated in FIG. 12 is designed to receive two fairly small stacks of packages 60 and 61 in side-by-side relation and therefore calls for an appropriately-dimensioned inner chamber. This is a more convenient arrangement for home use where the unit may be installed on a kitchen counter or placed within a wall cabinet. And instead of a hinged door as in FIG. 1, the unit includes a pair of sliding panels 62 and 63 of transparent plastic material having good thermal properties which reveal the contents of the chamber. Thus to obtain access to food in one stack of this unit, one slides one panel relative to the other, and to obtain access to the other stack, the panel movement is reversed.

In the double-ended unit shown in FIG. 13, the box incorporates two inner chambers 64 and 65, access to which is had through oppositely-disposed hinged doors 66 and 67. A double-ended fan 68 is provided, one for each chamber, the operation otherwise being the same as that of the unit in FIG. 6.

The unit shown in FIG. 14 is designed to function as a coin-operated vending machine to dispense, at a service temperature, pre-cooked meals of good quality. In this instance, the thermally-insulated box 69 is tall and narrow to accommodate a single, high stack of food packages, each on a separate open shelf to provide free spaces between the packages to admit hot air for heating the package.

The hinged door 70 of this unit, when opened, makes it possible to load the shelves with packages. Alternatively, the shelves may be formed on a portable wire frame which can be loaded with packages and then wheeled into the box. Door 70 is provided with a vertical row of hinged windows 71, 72, 73, etc. each of which, when opened, gives access to a single package on the same level in the box. A window can only be unlatched by depositing a coin or token in a slot 71a, 72s, 73s, etc. adjacent the window to actuate a latching mechanism in a manner conventional in vending machines.

Instead of a single stack vending machine unit, a multiple stack arrangement may be provided, an inner chamber being created for each stack, with common rear, top and front air spaces for all of these stacks to create the necessary plenums and main and feedback loops. In this way, the purchaser will be offered a large variety of pre-cooked meals to chose from.

The Electrical Control System

As shown in FIG. 15, the main heater element 55 and the auxiliary heater element 56 are both energized through a power line 75 having an on-off switch 76 therein which serves to turn on power for both elements. The line from switch 76 goes through a protective overload switch 77 into a thermal limit switch 78 which cuts off power to both heater elements should the heat in the unit exceed a pre-set value.

From limit switch 78 two line branches are extended, one leading to auxiliary heater section 56 through a thermostat switch 79, and the other leading to main heater section 55 through a controllable timer 80 and a thermostat switch 81. Associated with timer 80 is an indicator light 82, which is normally off and turns on only when the timer runs out. Timer 82 is provided with an operating button 83. The fact that the line power is switched on is indicated by a pilot light 94.

When power is turned on, auxiliary heater 56 is immediately energized, whereas main heater 55 is energized only after timer button 82 is pressed in. This timer is adjustable; and assuming that it takes one-half hour, using both heater elements, to bring the food in the oven to the service temperature level, say, at 150° F., then the timer is set for one-half hour, this being the heat-up phase. If desirable, timer 80 may also be arranged to control the operation of the motors for the air pump or fan and of the damper mechanism so that the fan and damper only operate in the heat-up phase.

At the end of the timing interval, timer 80 cuts off power to the main heater element 55 at which point the indicator light 83 turns on to give notice that meals are ready to be served. Thereafter, auxiliary heater 56 which remains operative under the control of thermostat 79 set to 150° F., which is the service temperature, functions to maintain the desired temperature level during the indefinite service phase.

While there have been shown and described preferred embodiments of a pulsating hot-air heat-up system in accordance with the invention, it will be appreciated that many changes and modifications may be made therein without, however, departing from the essential spirit thereof.

I claim:

1. A system for rapidly raising the temperature of a product having low thermal conductivity from a cold state to a hot state in which substantially the entire body of the product is at the same predetermined elevated temperature, said system comprising:
   A. a chamber having a product-receiving section flanked by an input plenum and an output plenum;
   B. a heater station;
   C. a fluid pump station;
   D. fluid conducting means connecting said fluid pump, said heater station, and said input and output plenums in series and defining a main flow loop with an input and output fluid flow portion whereby fluid drawn by said pump from the output plenum creates a negative pressure therein, the fluid being conducted through said heater station and being forced in the heated state into said input plenum to create a positive pressure therein, the resultant pressure differential causing fluid to flow at high velocity through said product receiving section to heat the product therein;
   E. bypass fluid conducting means forming a junction and joining portions of said main flow loop between said output flow portion and said input flow portion and forming a feedback loop, said feedback loop including said heating station and said fluid pump;
   F. control means to operate a damper mechanism;
   G. said damper mechanism located at said junction to cyclically block flow of fluid in said main loop through said chamber and to divert the flow into the by-pass means of said feedback loop to cause a pulsed fluid flow through said chamber whereby the flow in the chamber assumes the form of a pulsatory heat wave having pulses of fluid flow and relaxation intervals during which no fluid flows, said heat wave having a peak temperature above a predetermined level and a temperature below said predetermined level during said relaxation interval to effect a rapid heat transfer within the body of said product without, however, raising the internal temperature thereof substantially above said predetermined level.

2. A system as set forth in claim 1, wherein said heat-up phase is followed by a service phase in which the product is maintained at said predetermined temperature level.

3. A system as set forth in claim 2, further including a surface treatment phase during which phase said pulses have a still higher peak temperature to effect treatment of the surface of the product being heated.

4. A system as set forth in claim 1, wherein said fluid in said main loop is supplied to the input plenum through an input line and is fed from said output plenum to said heating station through an output line.

5. A system as set forth in claim 4, wherein said damper mechanism is constituted by a pivoted gate at said junction, which gate is oscillated to alternately block said input line and said bypass.

6. A system as set forth in claim 4, wherein said damper mechanism is constituted by a first rotating gate in said input line which in the course of rotation opens and closes said input line and a second rotating gate in said bypass which in the course of rotation opens said by-pass when the input line is closed and closes said by-pass when the input line is open.

7. A system as set forth in claim 4, wherein said damper mechanism is constituted by a stator and a rotor, each having an apertured disc and an apertured tube at right angles thereto, the apertures in said discs being phased with respect to the apertures in said tubes, whereby when the apertures in the rotor and stator discs of the rotor and stator are in registration, flow is permitted only through the input line, and when the apertures in the rotor and stator tubes are in registration flow is permitted only through the bypass.

8. A hot-air heating system for rapidly raising the temperature of a pre-cooked food from a cold or frozen temperature to a service temperature at which the food is in condition to be served, the pre-cooked food being stored in containers, said system comprising:
   A. a thermally insulated box having an access door, top, bottom and side walls,
   B. an inner chamber within the box for accommodating a stack of containers, said chamber including means for providing free spaces between said containers to admit heated air, said chamber further including an open front facing and spaced from said door, the space between the door and the open front defining an input plenum, a top wall forming an upper air space between the top of the box and said top wall, an outlet of said upper air space leads to said input plenum, said chamber further including a back wall having openings therein, said back wall forming a rear air space between said back wall and said side wall of the box, said rear air space defining an output plenum and forming an inlet to said upper air space, said input plenum, said output plenum and said upper air space defining a main flow path;
   C. means for forming a feedback path in the upper air space extending between the outlet and the inlet of this space;
   D. a heater assembly in said upper air space for heating air to a peak temperature well above said service temperature;
   E. suction means in said main flow path operating in conjunction with said heater assembly to draw air from the output plenum and to force this air through the upper air space into the input plenum to erect a heated air curtain therein and to create a pressure differential between the input and output plenums causing heated air to flow from the curtain through the back wall openings into the output plenum by way of the free spaces between the containers in the inner chamber at a relatively high velocity, the heated air being at the peak temperature well above the service temperature; and
   F. drive means for driving a gate means, said gate means in said main flow path and said feedback path operative in a heat-up phase to periodically divert the heated air from the outlet of the upper space into said feedback path for return to the inlet thereof to cause the air to be heated and recirculate in the upper space whereby the air admitted into the input plenum then takes the form of short periodic hot air pulses separated by no-flow intervals which bring about a rapid rate of heat transfer without, however, overheating the food in the containers subjected to these pulses, said pulses being at said peak temperature well above said service temperature, the air in the free spaces between the containers in the intervals between said pulses being at a temperature well below said peak temperature, the pulse rate being such that during said intervals heat from the outer layer of the food is transferred to the inner layers thereof to prevent said outer layer from reaching a temperature substantially above said service temperature.

9. A unit as set forth in claim 8, wherein said feedback path is defined by a horizontal septum in parallel relation to the top wall of the inner chamber.

10. A unit as set forth in claim 8, wherein said containers are formed by cardboard trays having a liquid-impermeable film laminated to the inner face thereof and a removable cover.

11. A unit as set forth in claim 8, wherein said heater assembly, when said food is heated to the service temperature at the completion of the heat-up phase, acts to maintain this temperature during a subsequent service phase.

12. A unit as set forth in claim 11, wherein said heater assembly is constituted by major and minor wattage electrical heaters, both heaters being operative in the heat-up phase, only the minor heater being operative in the service phase.

13. A unit as set forth in claim 12, including means to thermostatically control the heaters to generate hot air pulses in the heat-up phase whose temperature is about 190° F., and to maintain during the service phase a service temperature of about 150° F.

14. A unit as set forth in claim 8, wherein said suction means to draw air includes a fan disposed in said upper space driven by a motor external to said box.

15. A unit as set forth in claim 8, wherein said gate means is constituted by a rotating roll mounted across the junction of the outlet of the upper space and the front space, the roll having a cross-section defining an open sector which permits heated air to pass into the feedback path for a predetermined period in the course of each revolution, and a closed sector which thereafter blocks this path.

16. A unit as set forth in claim 15, wherein said roll has a semi-cylindrical form.

17. A unit as set forth in claim 15, wherein said roll rotates at a speed of about 2 RPM.

18. A unit as set forth in claim 8, wherein said inner chamber is dimensioned to accommodate at least two parallel stacks of containers.

19. A unit as set forth in claim 18, wherein said door is constituted by a pair of sliding panels providing access to said stacks.

20. A unit as set forth in claim 8, wherein said door is provided with a vertical array of hinged windows each of which, when opened, affords access to a correspondingly-positioned container in the stack.

21. A unit as set forth in claim 8, wherein each window operates in conjunction with a coin-actuated latching mechanism.

22. A unit as set forth in claim 8, in which a pair of inner chambers is disposed in the box in back-to-back relation to define a common output plenum, the open front of each chamber facing a respective door.

* * * * *